United States Patent [19]

Earls et al.

[11] Patent Number: 6,136,949
[45] Date of Patent: Oct. 24, 2000

US006136949A

[54] RESINS CONTAINING PHENYLETHYNL-TERMINATED COMPOUNDS

[75] Inventors: Jimmy Dan Earls; Bruce L. Burton; Brenda Thies Colegrove, all of Lake Jackson, Tex.

[73] Assignee: The Dow Chemical Company, Midland, Mich.

[21] Appl. No.: 09/146,403

[22] Filed: Sep. 3, 1998

[51] Int. Cl.[7] .................. C08G 73/10; C07D 307/77; C07D 407/00; C07D 493/02
[52] U.S. Cl. .................. 528/353; 528/125; 528/128; 528/171; 528/172; 528/173; 528/174; 528/176; 528/183; 528/185; 528/188; 528/220; 528/229; 528/350; 428/411.1; 264/45.1; 264/46.4; 264/510; 264/516; 549/243; 549/244
[58] Field of Search ............................ 528/353, 350, 528/229, 220, 176, 171, 172, 173, 174, 183, 185, 188, 125, 128; 428/411.1; 264/45.1, 46.4, 510, 516; 549/243, 244

[56] References Cited

U.S. PATENT DOCUMENTS

| | | | |
|---|---|---|---|
| 4,086,248 | 4/1978 | Arnold et al. | 549/232 |
| 4,532,270 | 7/1985 | Rossi et al. | 523/176 |
| 5,138,028 | 8/1992 | Paul et al. | 528/353 |
| 5,290,908 | 3/1994 | D'Alelio | 528/353 |
| 5,312,994 | 5/1994 | Bryant et al. | 568/306 |
| 5,344,982 | 9/1994 | Hergenrother et al. | 564/330 |
| 5,412,066 | 5/1995 | Hergenrother et al. | 528/353 |
| 5,426,234 | 6/1995 | Bryant et al. | 568/333 |
| 5,446,204 | 8/1995 | Bryant et al. | 568/333 |
| 5,493,002 | 2/1996 | McGrath et al. | 528/310 |
| 5,567,800 | 10/1996 | Hergenrother et al. | 528/353 |
| 5,599,993 | 2/1997 | Hergenrother et al. | 564/328 |
| 5,606,014 | 2/1997 | Connell et al. | 528/353 |
| 5,644,022 | 7/1997 | Jensen | 528/353 |
| 5,681,967 | 10/1997 | Hergenrother et al. | 549/243 |
| 5,689,004 | 11/1997 | Connell et al. | 564/328 |

OTHER PUBLICATIONS

Fang, Xiaomel et al, A Study of the Thermal Cure of a Phenylethynyl–Terminated Emide Model Compound and a Phenylethynyl–Terminated Imide Oligomer (PETI–5), Journal of Polymer Science: Part A: Polymer Chemistry, vol. 36, pp. 461–470 (1998).

Harrington, Karen A. et al., "Characterization of Cure Chemistry of Selected Phenylethynyl–Terminated Polyimides and Model Compounds", 41ST International Sampe Symposium, pp. 135–148 (Mar. 24–28, 1996).

Hergenrother, P. M. et al., "Chemistry and Properties of Imide Oligomers End–Capped with Phenylethynylphtalic Anhydrides", Polymer, vol. 35, No. 22, pp. 4857–4864 (1994).

Meyer, G. W. et al., "Synthesis and Characterization of Polymides Endcapped with Phenylethynylphthalic Anhydride", Journal of Polymer Science: Part A: Polymer Chemistry, vol. 33, pp. 2141–2149 (1995).

Wood, Karen H. et al., "Cure Chemistry of Phenylethynyl Terminated Oligomers", 42nd International Sampe Symposium, pp. 1271–1282 (May 4–8, 1997).

Primary Examiner—P. Hampton-Hightower

[57] ABSTRACT

A compound of the formula:

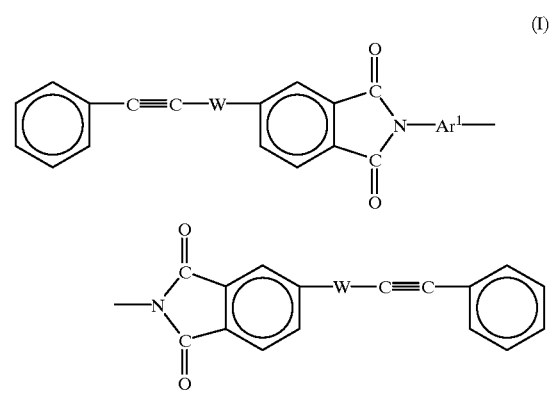

(I)

wherein $Ar^1$ is the backbone of any aromatic diamine moiety other than 3,4'-oxydianiline and W independently in each occurrence is a bond or a radical selected from the group consisting of:

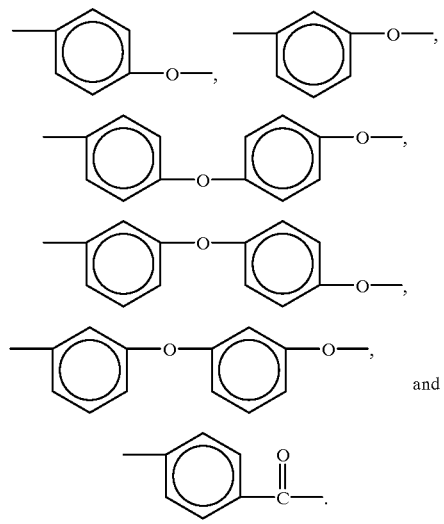

and

19 Claims, No Drawings

RESINS CONTAINING PHENYLETHYNL-TERMINATED COMPOUNDS

BACKGROUND OF THE INVENTION

This invention relates to polyimide resins prepared from aromatic diamines and phenylethynyl phthalic anhydride or phenylethynyl-substituted phthalic anhydrides. These polyimide resins have very low melt viscosities and, when cured, have good mechanical properties and are stable at very high temperatures.

Certain aromatic polyimides are known for their exceptional thermal, thermooxidative, and chemical resistance. These polymers are typically prepared by the polymerization of aromatic diamines and dianhydrides in a 2-step synthesis, first to form a poly(amide acid) precursor, which is then cyclodehydrated to the corresponding polyimide, as described in Hergenrother and Smith, "Chemistry of Imide Oligomers End-capped with Phenylethynylphthalic Anhydrides", Vol. 35, Polymer, p. 4857 (1994). However, such resins are difficult to melt process due to their high melting temperatures and viscosities which restrict their use in structural adhesive and composite applications. The melt processability of such oligomers or polymers may be altered, for example, by the incorporation of flexible segments or by making low molecular weight oligomers which are end-capped with reactive groups. However, the viscosities of these different types of oligomers and polymers may still be relatively high.

If an end-capping compound is used, such compound typically also contains a latent-curable reactive group in addition to the group which caps the oligomer or polymer, which reacts with other end groups in the resin at high temperatures. An article may be prepared by, for example, processing the uncured resin into a desired shape, and then heating the resin to cause the end groups to react and cure the resin. The use of end-capping agents with latent-curable groups provides a means to chain-extend or crosslink the polymer at high temperatures, which increases the Tg of the cured polymer. One type of end group that has been used for this purpose is the phenylethynyl end group, as described in U.S. Pat. Nos. 5,599,993 and 5,493,002. Another approach has been to locate the phenylethynyl groups pendant to the oligomer backbone, by means of a trifunctional aryl compound having two diamine groups and one phenylethynyl group, as disclosed in U.S. Pat. No. 5,689,004. These pendant end groups have been found to be stable under the polyimide synthesis conditions, and at temperatures of up to 250° C. Such pendant groups will then react and cure at temperatures above about 300° C., resulting in a polymer with a higher Tg than that of a resin that was not prepared using the phenylethynyl pendant groups. Phenylethynyl phthalic anhydride end-capping reagents are described in U.S. Pat. No. 5,567,800. However, the melting temperatures and the melt viscosities of the above-described oligomers having pendant or terminal phenylethynyl groups may be too high for certain methods of processing. Another approach to lowering the melt viscosity of the resin has been to add reactive diluents having two phenylethynyl end groups, as described in U.S. Pat. No. 5,426,234. However, reactive diluents may adversely affect the thermal and physical properties of the cured polymer, such as by reducing its Tg or toughness.

The low melt viscosities obtained for the compositions of this invention are particularly useful in the preparation of high performance composites via resin transfer molding. Resin transfer molding is a process that utilizes a preform, which consists of multiple plies of graphite, glass or other reinforcing fiber. This preform is placed in a mold, which is then filled with a thermosetting resin that infiltrates and wets the fibers of the preform. This process of consolidating the fiber and the resin may be aided by the use of pressure. After this step, the resin is then cured to produce a composite part. Composite parts produced by resin transfer molding are typically less expensive to make than those obtained by other methods, such as those using prepregs, due to the fact that resin transfer molding is not as labor intensive. Resin transfer molding requires the use of thermosetting resins which have a low melt viscosity to permit filling the mold, which can be of a complex shape, and to infiltrate and wet out the preform, which may be comprised of multiple layers of fibers. In addition to having a low viscosity, resins used in resin transfer molding need to have cured resin properties such that the parts produced are of a relatively high strength, stable at high temperatures and are not too brittle.

SUMMARY OF THE INVENTION

One aspect of this invention is a thermosetting resin composition of the formula:

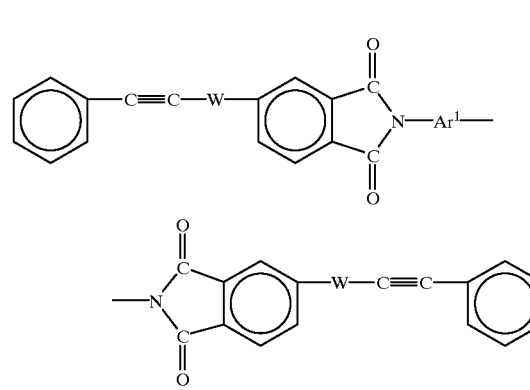

wherein $Ar^1$ is the backbone of any aromatic diamine moiety other than 3,4'-oxydianiline and W independently in each occurrence is a bond or a radical selected from the group consisting of:

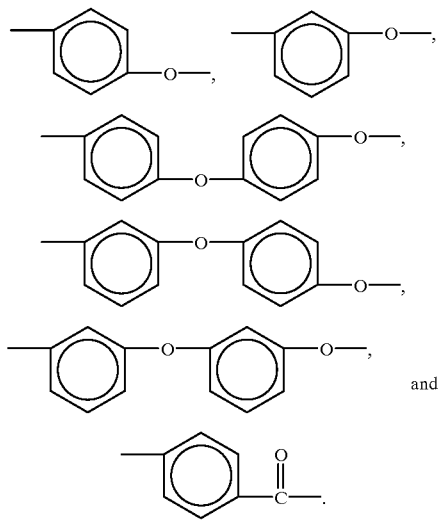

Another aspect of this invention is a cured polymer obtained by heating a plurality of the compounds of Formula (I), optionally with other oligomers or polymers having terminal phenylethynyl groups.

Another aspect of this invention is a process for preparing a thermosetting resin composition comprising reacting a compound of the formula $NH_2-Ar^2-NH_2$, a phenylethynyl-terminated phthalic anhydride, and a dianhydride, and optionally, a triamine compound in molar proportions so that at least 10 percent by weight of the composition is a compound of the formula:

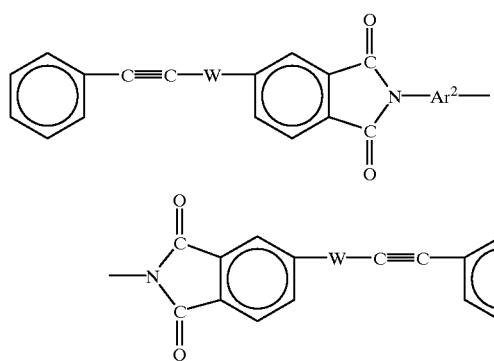
(II)

wherein $Ar^2$ is the backbone of any aromatic diamine moiety and W is a bond or a radical selected from the group consisting of:

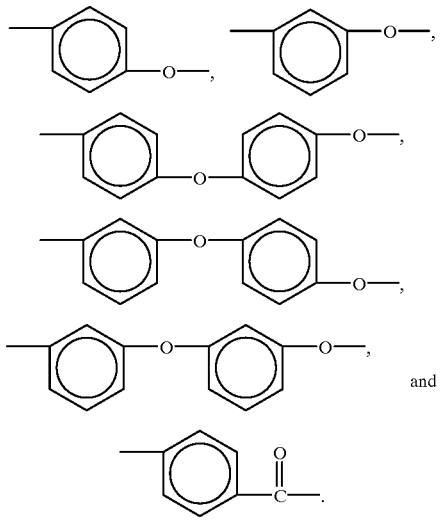

and

In a fourth aspect, this invention is a process for preparing a composite article, comprising:
(a) placing a preform in a mold;
(b) contacting the preform with a thermosetting resin composition having a melt viscosity of less than 1000 centipoise at a temperature above its melting point;
(c) heating and compressing the resin composition and preform under conditions sufficient to cause the composition to saturate the preform and then cure, thereby forming the article; and
(d) cooling the mold and removing the article from the mold;
wherein the resin composition comprises at least 10 percent by weight of a compound of Formula (II).

Another aspect of this invention is the cured, composite article obtained from the above process.

It has been discovered that the compounds of the invention are useful in preparing thermosetting resins. Depending on the particular formulations, such resins may have a relatively low melt viscosity. Such resins are particularly useful in the preparation of composite parts using resin transfer molding techniques. Surprisingly, when this thermosetting resin is cured at high temperatures to form a fiber-containing composite, the resulting part has a high shear strength, is stable at high temperatures and is not too brittle. In addition, these compounds may be used by themselves as a one component resin, which may have significant manufacturing and cost advantages over a multi-component formulation containing higher molecular weight oligomers and polymers, reactive diluents, and separate crosslinking compounds. These and other advantages of the invention will be apparent from the description that follows.

DETAILED DESCRIPTION OF THE INVENTION

The term "backbone of any aromatic diamine moiety" as used herein refers to the chemical structure of any aromatic diamine without the terminal amine groups. In Formulas (I) and (II), $Ar^1$ and $Ar^2$ are preferably selected from:

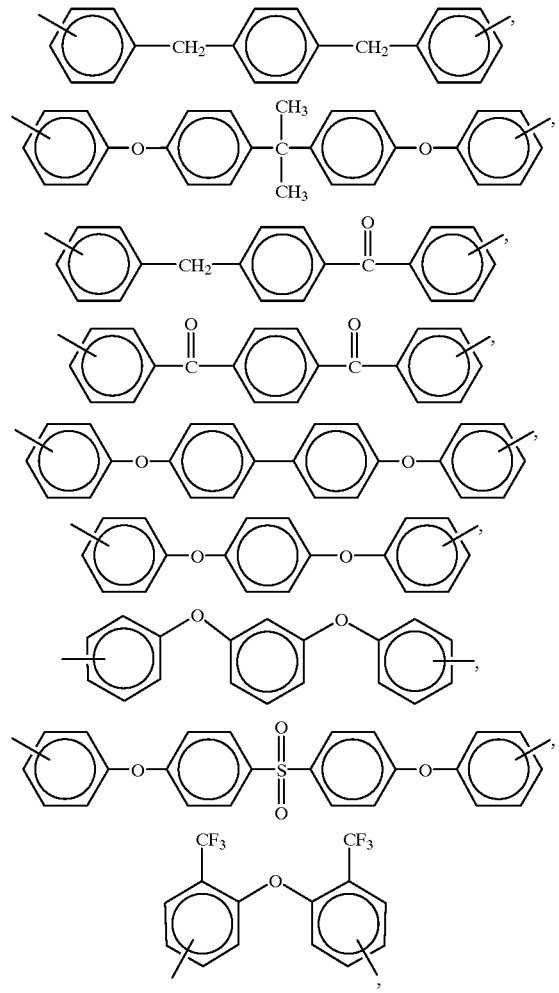

-continued

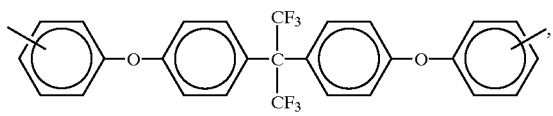

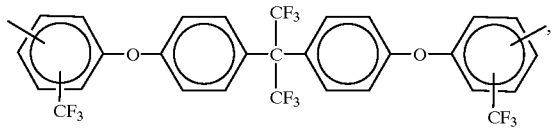

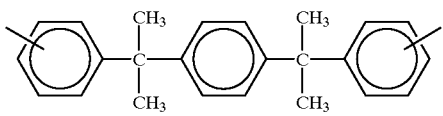

and

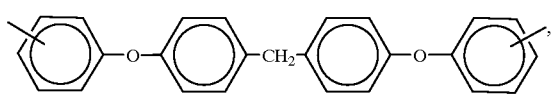

and are most preferably selected from:

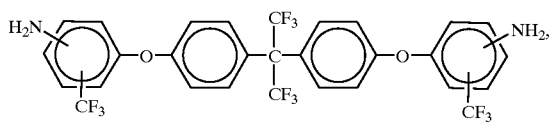

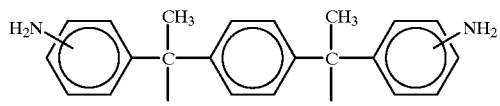

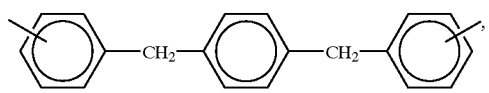

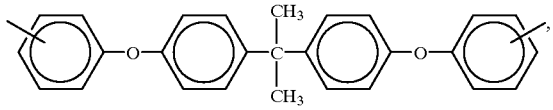

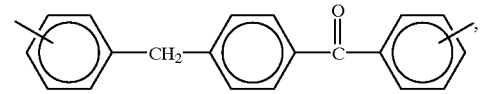

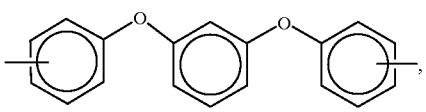

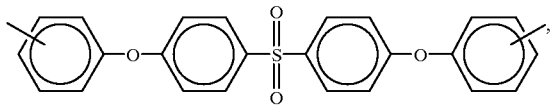

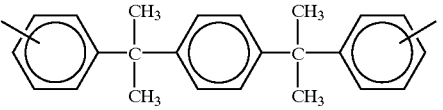

and

-continued

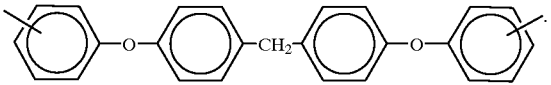

W is preferably a single bond or

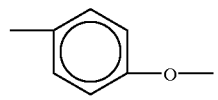

and is most preferably a single bond (that is, the groups shown on either side of W in Formula (II) are bonded directly to each other).

The compounds of the invention may be prepared by any suitable process, but are preferably prepared by reacting phenylethynyl phthalic anhydride or a phenyethynyl-substituted phthalic anhydride with a diamine or a combination of two or more diamines of the formula $NH_2$—$Ar^1$—$NH_2$ in a molar ratio of at least 2:1. Examples of diamines that may be used in such a process include, but are not limited to, those of the formulas:

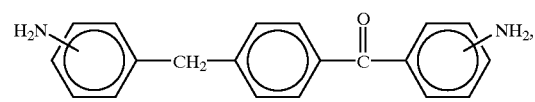

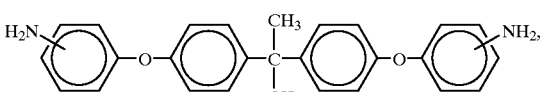

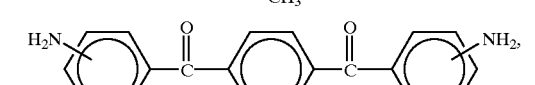

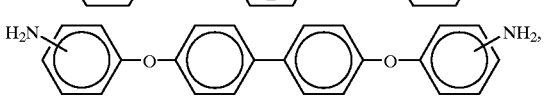

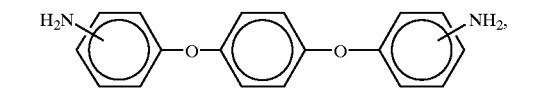

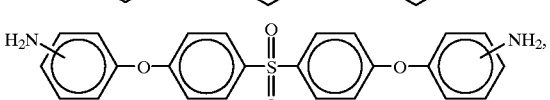

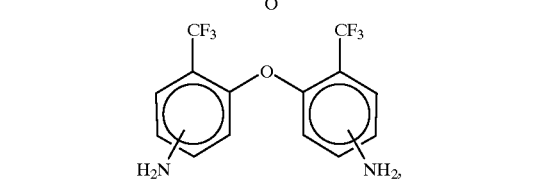

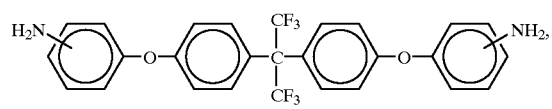
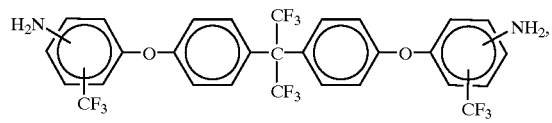
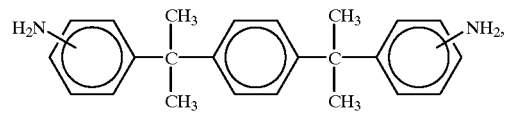
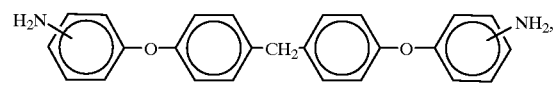
and
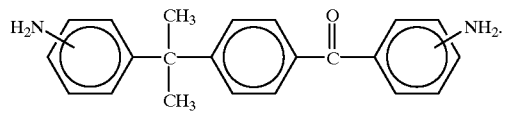
Examples of suitable phenylethynyl-substituted phthalic anhydrides include, but are not limited to, those of the formulas:
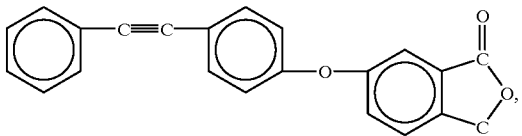
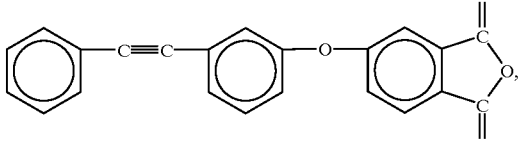
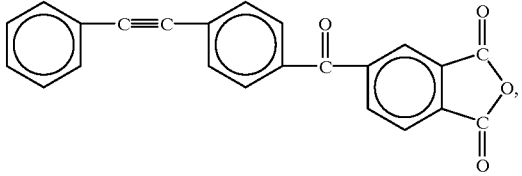
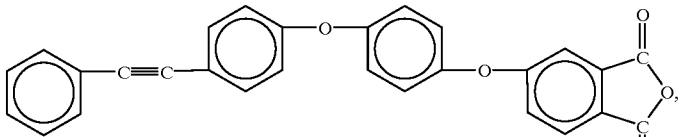
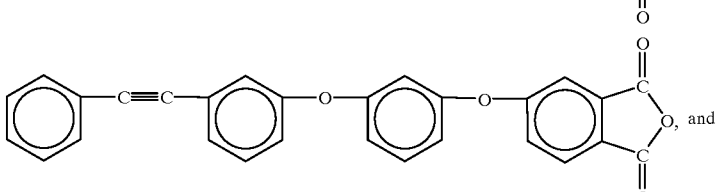
and
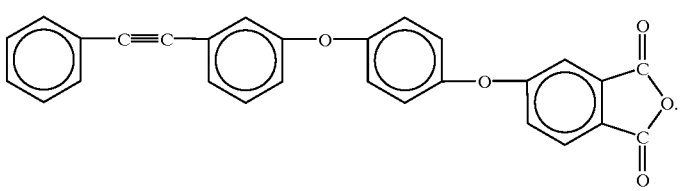

The reaction between the diamine and the phenylethynyl phthalic anhydride may be carried out under any conditions that will allow the reaction to proceed. The preferable method of synthesis is to first form an amide acid precursor by reacting the aromatic diamine and the phenylethynyl phthalic anhydride or phenylethynyl-substituted phthalic anhydride in a solvent such as 1-methyl-2-pyrrolidinone at temperatures from about 25° C. to about 80° C. This amide acid precursor is then converted to the imide compound by thermal cyclodehydration in 1-methyl-2-pyrrolidinone using toluene to azeotropically distill off the water formed. This step is preferably done at a temperature in the range of from about 150° C. to about 170° C.

In another embodiment, the compound of the invention may be prepared in situ in a reaction mixture of diamine, phenylethynyl phthalic anhydride, aromatic dianhydrides and, optionally, aromatic triamines which also permit the formation of phenylethynyl-terminated oligomers and polymers. This is done by creating a stoichiometric imbalance between the diamine and the dianhydride (that is, using an amount of dianhydride sufficient to react with a portion of the diamine present in the reaction mixture and form oligomers and/or polymers, while leaving sufficient diamine available in the reaction mixture to react with a phenylethynyl phthalic anhydride to form the compounds of the invention). The preferred stoichiometric amounts of diamine and dianhydride is such that preferably from about 10 to about 90 weight percent of the composition consists of the Formula (II) compound. Examples of dianhydrides which may be used are those of any aromatic tetracarboxylic acid such as 1,2,4,5-benzenetetracarboxylic dianhydride, 3,3',4,4'-benzophenonetetracarboxylic dianhydride, 3,3',4,4'-biphenyltetracarboxylic dianhydride, 4,4'-oxydiphthalic anhydride and 3,3',4,4'-diphenylsulfone tetracarboxylic dianhydride. Preferably, such dianhydrides are used to provide oligomers in an amount, based on the weight of the composition, of at least 10 percent, more preferably at least 50 percent; and preferably no greater than 90 percent. Examples of triamines which may be optionally used to provide branching of the diamine and dianhydride oligomers are 2,4,6-triaminopyrimidine, 1,3,5-tris(4-aminophenoxy)benzene and 2,4-bis(p-aminobenzyl)aniline. Preferably, such triamines are used in an amount, based on the weight of the composition, of at least 1 percent, more preferably at least 2 percent; and preferably no greater than 20 percent, more preferably no greater than 10 percent. The low viscosities and processing temperatures of these compositions aid their use in the manufacture of parts.

In the first step of the process of the invention, a preform is placed in a mold. The term "preform" as used herein refers to an article comprised of at least 80 percent by weight of fibers such as glass, aramid, or carbon fibers. Preferably, the preform comprises at least 90 percent by weight of fibers, and most preferably at least 95 percent. A small amount of a thermoplastic or thermosetting resin may be optionally utilized to hold in place and bond multiple plies of the fiber together.

In step (b) of the process of the invention, the preform is contacted with a resin having a melt viscosity of less than 1000 centipoise (cps) and containing at least 10 percent by weight of the compound of Formula (II). The optimal amount of the compound used in a formulation will be determined by the melt viscosity and/or processing temperature requirements of the particular process in which the formulation is to be used. The resin used in the process of the invention has a melt viscosity of less than 1000 cps, preferably less than 500 cps, more preferably less than 300 cps. The resin is preferably utilized in an amount sufficient to provide optimum physical properties, but is preferably at least 30 percent by weight of the final part, more preferably at least 45 percent; and preferably no greater than 70 percent, more preferably no greater than 50 percent.

In step (c) of the process of the invention, the resin and preform are first heated and compressed under conditions sufficient to cause the resin to saturate the preform and consolidate the part. The temperature and pressure necessary to carry out this step will depend on the particular resin, the type of fibers, and the thickness of the preform. However, the temperatures and pressures are typically in the range of 150° C. to 315° C. and 50 psi to 200 psi, respectively. It is preferable to minimize the temperature in the mold until the preform is sufficiently saturated, so that it does not undergo more than a minimal amount of cure during that time, which may prevent further infiltration of the perform. Preferably, the preform and resin are heated at a temperature of less than about 300° C. during this saturation step.

Next, the preform and resin are heated for an additional period of time to cause the resin to cure, thereby forming the composite article. The temperature used to cure the resin is preferably at least 280° C., more preferably at least 320° C., most preferably at least 350° C; but is preferably no greater than 400° C., more preferably no greater than 375° C., most preferably no greater than 350° C. In step (d) of the process of the invention, the mold is cooled and the article is removed therefrom.

Cured resins and composite articles prepared by the process of the invention have good shear strength as measured by ASTM Method D-2344 (1992) and high glass transition temperatures as measured by Differential Scanning Calorimetry (DSC) using ASTM Method D-3418-82 (1988) and Dynamic Mechanical Thermal Analysis (DMTA). Such articles are useful as structural components which can withstand temperatures of up to 350° C. One application in this area is as a lighter weight alternative to titanium components in aircraft engines. In addition to composites, other potential applications for the compositions of this invention include high temperature films, coatings and adhesives.

ILLUSTRATIVE EMBODIMENTS

EXAMPLE 1

Preparation of a Phenylethynyl-terminated Resin Composition Number 1:

1,3 bis(3-aminophenoxy)benzene (25 grams; 0.0855 moles) is added to a 250 milliliter round bottom flask equipped with a stirrer, nitrogen purge, water cooled condenser, thermometer and heating mantel connected to a temperature controller. 1-methyl-2-pyrrolidinone (52.203 grams) is next added to the round bottom flask and stirring is started. In a 250 milliliter beaker, 1-methyl-2-pyrrolidinone (52.493 grams) and 4-phenylethynyl phthalic anhydride (42.458 grams; 0.171 moles) are combined and stirred. After obtaining a slurry in the beaker, its contents are added to the 250 milliliter flask. An additional 52.472 grams of 1-methyl-2-pyrrolidinone is added to the 250 milliliter flask during the transfer of the beaker contents. After the addition of the 4-phenylethynyl phthalic anhydride slurry to the flask, the mixture self heats to 45° C. and turns clear. This solution is then heated to 70° C. where it is maintained for 21 hours. After 21 hours at 70° C., a 15 milliliter Dean-Stark distillation receiver filled with toluene is installed on the top of the round bottom flask beneath the condenser. Toluene (30.528 grams) is then added directly to the 250 milliliter round bottom flask. This solution is then heated to 160° C. where it is maintained for 18 hours. After 18 hours at 160° C., the Dean-Stark receiver contains a bottom, aqueous layer of 5.2 milliliters. This is drained along with the total contents of the Dean-Stark receiver. The solution in the round bottom flask is then heated to 200° C. where it is maintained for 2 hours. During this time, the Dean-Stark receiver is drained an additional time. After 2 hours at 200° C., the solution is cooled to 70° C. and then slowly poured into an operating blender containing 350 milliliters of water. On addition of the contents of the round bottom flask to the water, a light brown precipitate forms. After blending for 15 minutes, the solution is filtered using a fritted glass filtering funnel (ASTM 10–15M). The wet filter cake obtained is added to an operating blender containing 275 milliliters of fresh water. Additional water is added during the washing of the filter funnel contents into the blender. After this wash, the total content of the blender is approximately 1.25 liters. After blending for 15 minutes, the solution is filtered using the same fritted glass filtering funnel. The filter cake obtained from the second filtration is added back to the blender, which contains 300 milliliters of fresh water. After washing the contents of the filtering funnel into the blender with additional water, the total volume in the blender is approximately 0.75 liters. This solution is blended for 15 minutes and then filtered. The filter cake obtained is first dried at 120° C. in a vacuum oven for 16 hours. This material is then ground to a coarse powder and placed back in the vacuum oven where it is dried for an additional 12 hours at 212° C. The dried, fused powder is then allowed to cool to room temperature under vacuum. After cooling to room temperature, the resin is reground to a fine powder using a mortar and pestle.

Analysis of Phenylethynyl-terminated Resin Number 1:

Differential scanning calorimetry (DSC) analysis is conducted for an 11.6 milligram sample of the resin prepared from above using a heating rate of 10° C. per minute and a nitrogen purge of 35 cubic centimeters per minute. This DSC analysis shows that the resin prepared had a glass transition temperature of 102° C., a melting endotherm with a peak of 217° C., and a cure exotherm with an onset of 301° C., peak of 390° C. and a total energy of 328 joules per gram. Viscosity measurements for the resin are conducted using 2 inch parallel plates at 100 radians per second, 10 percent strain and a heating rate of 2° C. per minute. These measurements show a minimum viscosity of 22 cps at 497° F. (258° C.) following melt. Viscosity measurements versus time are also made for the resin at 260° C. These measurements show no change in viscosity after 4 hours.

Preparation and Analysis of Cured Resin:

The above resin (7.575 grams), contained in an aluminum pan, is placed in a convection oven, which is preheated to 300° C. After 21 hours at 300° C., the oven temperature is increased to 350° C. After the resin has been in the 350° C. oven for 4 hours it is removed and cooled to room temperature. On cooling to room temperature, a cured resin casting is obtained from the aluminum pan. Weighing of this casting shows that a 1.3 percent weight loss has occurred during cure. Visible examination of the casting shows no indication of voids. A 15 milligram sample of the casting is taken for DSC analysis at a heating rate of 10° C. per minute and using a nitrogen purge of 35 cubic centimeters per minute. This analysis shows an inflection at 301° C., which is taken as the glass transition temperature for the cured polymer. The cured polymer obtained is next placed in a 650° F. (343° C.), forced air convection oven for approximately 9 hours during the day followed by a lower, overnight, temperature exposure to 257° F. (125° C.) in another forced air convection oven. This cycle is repeated multiple times. After 36 hours of total exposure to 650° F., a 1.018 weight percent loss is observed. Also at 36 hours, the surface of the casting looks good and there is no evidence of cracking or loss of gloss.

Structure of Phenylethynyl-terminated Resin Number 1:

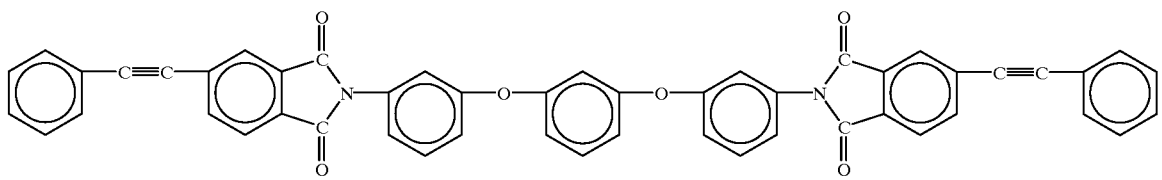

Preparation of a Carbon Fiber Reinforced Composite Using Phenylethynyl-terminated Resin Number 1:

The manufacture of a carbon fiber reinforced composite is done using an infusion resin flow mold (IRFM). This mold is a three part, tool steel mold consisting of a flat base plate, picture frame spacer plate, and a picture frame clamping plate. Before assembly of the mold, the mold parts are cleaned, polished and mold released. The mold parts are cleaned using a liquid abrasive applied with a scouring pad in conjunction with an orbital sander. After debris and steel discoloration have been removed from the mold surfaces, acetone is used to clean away the liquid abrasive. A mold polish paste is then applied to the mold surfaces using a clean cloth in conjunction with an orbital sander to obtain a mirror-like surface finish. The mold parts are then wiped down with acetone before application of the mold release agent. The mold release agent is generously applied to all mold surfaces and allowed to air dry before the application of subsequent coats. Four coats of mold release agent are applied to the mold surfaces. To effectively adhere the mold release onto the metal surfaces, the mold parts are placed in an oven for 15 minutes at about 100° C. Lastly, a polyimide film, which is used as a diaphragm, is prepared by punch cutting a bolt hole pattern present on the picture frames, and curing four coats of mold release agent onto one side.

The infusion resin flow mold is assembled in the following manner. The flat base plate is placed on a flat working surface with the clean side up. A silicone rubber cord is next placed into a machined o-ring seat in the picture frame spacer plate. This spacer plate is placed onto the base plate with the red silicone cord between them creating a seal. At this point, the resin, which is in powder form, is placed into the mold cavity formed thus far. Based on the preform weight and the desired fiber volume, 59.59 grams of powdered resin is used. This powdered phenylethynyl-terminated resin is prepared from 1,3-bis(3-aminophenoxy) benzene and 4-phenylethynyl phthalic anhydride. The carbon fiber preform is then placed in the mold on top of the powdered resin. The carbon fiber used in the manufacture of the composite is an IM7, 6K, GP, 4HS with an areal weight of 200.2 grams/m$^2$. The carbon fiber is cut to 5 inches×7 inches, stacked by aligning each ply using the fabric tracers, and then sewn together to fix the orientation. The weight of this sewn, 16-ply preform is 64.71 grams. On the top side of the spacer plate is a machined groove, which accommodates a 1/16-inch PEEK tube that is used to apply vacuum to the constructed cavity. A malleable tacky tape is placed in this groove and along the inner edge on the top side of the picture frame spacer plate. This tacky tape creates a seal between the spacer plate and the polyimide film diaphragm creating the sealed cavity in which the resin charge and carbon fiber preform are enclosed. After the diaphragm is placed onto the tacky tape seal, the picture frame clamping plate is positioned onto the mold assembly and bolted down tightly compressing the tacky tape and silicone rubber seals.

After the mold has been sealed, a vacuum is applied to about 400 millitor. The mold is then placed into a mechanical press and a thermocouple in the baseplate of the mold is connected to a Camille™ data acquisition unit. An anvil is then placed on top of the diaphragm and the mold program is started. The mold program used in the manufacture of the panel is as follows:

| Duration (min) | Temperature (° C.) | Pressure (psi) |
| --- | --- | --- |
| 10 | 260 | 15 |
| 360 | 260 | 50 |
| 720 | 280 | 50 |

After the press has been pressured to 50 psi at 260° C., a resin breach in the gasket seals occurs. At this point the platens are opened just enough to relieve pressure on the consolidated composite and the program is completed. The composite is then removed from the mold and post cured for 2 hours at 300° C., 1.5 hours at 325° C. and 3 hours at 350° C. in convection oven.

Analysis of the Composite Panel:

After completing the post cure in a convection oven, the composite is cut to observe the quality of the consolidation. The cross section reveals very little to no voids. The composite has an average part thickness of 0.2735 centimeter (0.1077 inch) and a fiber volume of 65.8 percent. A 19.8 milligram sample of the neat resin from the composite flash is analyzed by DSC with a nitrogen purge of 35 centimeters/minute at a heating rate of 10° C. per minute to 450° C. This analysis shows an inflection at 285° C., which is taken as the glass transition temperature for the composite.

A portion of the composite is mechanically tested for short beam shear strength using ASTM D-2344 (1992). Nine samples are cut from the composite and tested. The results of these tests showed that the composite had a short beam shear strength of 9380 psi with a standard deviation of 662 psi and a coefficient of variation of 7.06 percent.

EXAMPLE 2

Preparation of Phenylethynyl-terminated Resin Composition Number 2:

1-methyl-2-pyrrolidinone (116.690 grams) is added to a stirred, 250 milliliter round bottom flask equipped with a nitrogen purge, water cooled condenser, thermometer and heating mantel connected to a temperature controller. Bis (4-[4-aminophenoxy]phenyl)sulfone (35 grams; 0.0809 moles) is next added to the round bottom flask. After the bis(4-[4-aminophenoxy]phenyl)sulfone has dissolved, 4-phenylethynyl phthalic anhydride (40.175 grams; 0.1618 moles) and an additional 58.740 grams of 1-methyl-2-pyrrolidinone are added to the 250 milliliter flask. After the addition of the 4-phenylethynyl phthalic anhydride and the 1-methyl-2-pyrrolidinone, the mixture self heats to 43° C. and is clear. This solution is then heated to 70° C. where it is maintained for 16 hours. After 16 hours at 70° C., a 15 milliliter Dean-Stark distillation receiver filled with toluene is installed on the top of the round bottom flask beneath the condenser. Toluene (34.043 grams) is also added directly to the 250 milliliter round bottom flask. This solution is then heated to 160° C. where a precipitate forms. After the formation of the precipitate, more 1-methyl-2-pyrrolidinone (16.754 grams) is added. After 22 hours at 160° C., the Dean-Stark receiver contains a bottom, aqueous layer of 3.0 milliliters. This is drained along with the total contents of the Dean-Stark receiver. The solution in the round bottom flask is then heated to 200° C. where it is maintained for 2 hours. During this time the Dean-Stark receiver is drained an additional two times. After 2 hours at 200° C., the solution is cooled to 80° C. and then slowly poured into an operating blender containing 350 milliliters of water. After blending for 15 minutes, the solution is filtered using a fritted glass filtering funnel (ASTM 10–15M). The wet filter cake obtained is placed back in the blender and fresh water is added. After the addition of the water, the total volume in the blender is approximately 750 milliliters. After blending for 15 minutes, the solution is filtered using the same fritted glass filtering funnel. The filter cake obtained from the second filtration is added back to the blender along with more fresh water. The total volume in the blender after this addition is approximately 650 milliliters. This solution is blended for 15 minutes and then filtered. The filter cake obtained is placed in a 112° C., forced air convection oven for 1.5 hours. This material is then ground to a coarse powder and placed in a vacuum oven where drying is continued for an additional 15 hours at 123° C. and 13 hours at 214° C. The dried powder is then allowed to cool to room temperature under vacuum. After cooling to room temperature, the resin is reground to a fine powder using a mortar and pestle.

Analysis of Phenylethynyl-terminated Resin Number 2:

Differential scanning calorimetry (DSC) analysis is conducted for an 8.83 milligram sample of the resin prepared from above using a heating rate of 10° C. per minute and a nitrogen purge of 35 cubic centimeters per minute. This DSC analysis showed that the resin prepared had a melting endotherm with a peak of 334° C. and a cure exotherm with an onset of 338° C., peak of 369° C. and a total energy of 306 joules per gram.

Preparation and Analysis of Cured Resin:

The above resin (4.060 grams), contained in an aluminum pan, is placed in a convection oven that is preheated to 300° C. After 18 hours at 300° C., the oven temperature is increased to 350° C. After the resin has been in the 350° C. oven for 4 hours, it is removed and cooled to room temperature. On cooling to room temperature, a cured resin casting is obtained from the aluminum pan. Weighing of this casting shows that a 2.9 percent weight loss has occurred during cure. A 15 milligram sample of the casting is taken for DSC analysis at a heating rate of 10° C. per minute and using a nitrogen purge of 35 cubic centimeters per minute. This analysis showed an inflection at 371° C., which was taken as the glass transition temperature for the cured polymer.

Structure of Phenylethynyl-terminated Resin Number 2:

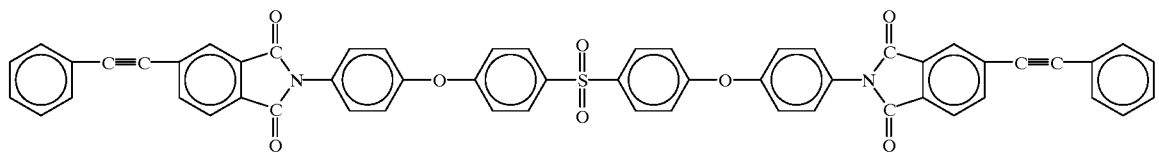

Analysis of Phenylethynyl-terminated Resin Number 3:

DSC analysis is conducted for an 8.74 milligram sample of the resin prepared from above using a heating rate of 10° C. per minute and a nitrogen purge of 35 cubic centimeters per minute. This DSC analysis shows that the resin prepared has a melting endotherm with a peak of 273° C. and a cure exotherm with an onset of 326° C., peak of 370° C. and a total energy of 326 joules per gram. Viscosity measurements for the resin are conducted using 2 inch parallel plates at 100 rads per second, 10 percent strain and a heating rate of 2° C. per minute. These measurements showed a minimum viscosity of 10 centipoise at 518° F. (270° C.) following melt.

Preparation and Analysis of Cured Resin:

The above resin (3.061 grams), contained in an aluminum pan, is placed in a convection oven that is preheated to 300° C. After 16 hours at 300° C., the oven temperature is increased to 350° C. After the resin has been in the 350° C. oven for 3 hours it is removed and cooled to room temperature. On cooling to room temperature, a cured resin casting is obtained from the aluminum pan. Weighing of this casting shows that a 0.7 percent weight loss had occurred during cure. A 33.5 milligram sample of the casting is taken for DSC analysis at a heating rate of 10° C. per minute and using a nitrogen purge of 35 cubic centimeters per minute. This analysis showed an inflection at 325° C., which was taken as the glass transition temperature for the cured polymer.

Structure of Phenylethynyl-terminated Resin Number 3:

EXAMPLE 3
Preparation of Phenylethynyl-terminated Resin Composition Number 3:

Bis(4-[3-aminophenoxy]phenyl)sulfone (32 grams, 0.0740 moles) is added to a stirred, 250 milliliter round bottom flask equipped with a nitrogen purge, water cooled condenser, thermometer and heating mantel connected to a temperature controller. 1-methyl-2-pyrrolidinone (106.559 grams) is next added to the round bottom flask. After the bis(4-[3-aminophenoxy]phenyl)sulfone has dissolved, 4-phenylethynyl phthalic anhydride (36.732 grams; 0.1480 moles) and an additional 53.517 grams of 1-methyl-2-pyrrolidinone are added to the 250 milliliter flask. After the addition of the 4-phenylethynyl phthalic anhydride and the 1-methyl-2-pyrrolidinone, the mixture self heats to 43° C. and is clear. This solution is then heated to 70° C. where it is maintained for 23 hours. After 23 hours at 70° C., a 15 milliliter Dean-Stark distillation receiver filled with toluene is installed on the top of the round bottom flask beneath the condenser. Toluene (31.285 grams) is also added directly to the 250 milliliter round bottom flask. This solution is then heated to 160° C. After 19.5 hours at 160° C., the Dean-Stark receiver contains a bottom, aqueous layer of 4.4 milliliters. This is drained along with the total contents of the Dean-Stark receiver. The solution in the round bottom flask is then heated to 200° C. where it is maintained for 2 hours. During this time, the Dean-Stark receiver was drained an additional one time. After 2 hours at 200° C., the solution is cooled to 70° C. and then slowly poured into an operating blender containing 350 milliliters of water. After blending for 15 minutes, the solution is filtered using a fritted glass filtering funnel (ASTM 10–15M). The wet filter cake obtained is placed back in the blender and fresh water is added. After the addition of the water, the total volume in the blender is approximately 600 milliliters. After blending for 15 minutes, the solution is filtered using the same fritted glass filtering funnel. The filter cake obtained from the second filtration is added back to the blender along with more fresh water. The total volume in the blender after this addition is approximately 600 milliliters. This solution is blended for 15 minutes and then filtered. The filter cake obtained is placed in a 112° C., forced air convection oven for 3 hours. This material is then ground to a coarse powder and placed in a vacuum oven where drying is continued for an additional 14.5 hours at 121° C. and 13 hours at 214° C. The dried powder is then allowed to cool to room temperature under vacuum. After cooling to room temperature, the resin is reground to a fine powder using a mortar and pestle.

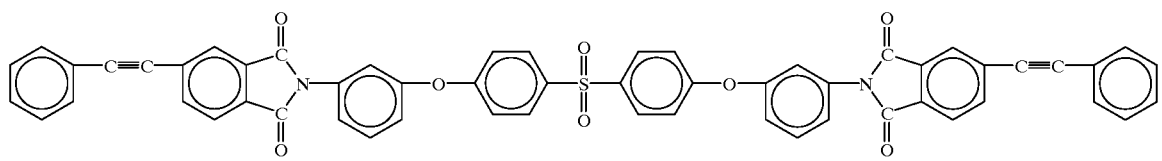

Preparation of a Carbon Fiber Reinforced Composite Using Phenylethynyl-terminated Resin Number 3:

The infusion resin flow mold used to prepare the composite is the same as that used in Example 1. Based on the preform weight and the desired fiber volume of 53 percent, 59.4 grams of powdered resin is used. This powdered phenylethynyl-terminated resin is prepared from bis(4-[3-aminophenoxy]phenyl)-sulfone and 4-phenylethynyl phthalic anhydride. The carbon fiber preform is then placed in the mold on top of the powdered resin. The carbon fiber used in the manufacture of the composite is an IM7, 6K, GP, 4HS with an areal weight of 200.2 grams/m². The carbon fiber is cut to 5 inches×7 inches, stacked by aligning each ply using the fabric tracers, and then sewn together to fix the orientation. The weight of this sewn, 16-ply preform is 66.64 grams. On the top side of the spacer plate is a machined groove, which accommodates a 1/16-inch PEEK tube that is used to apply vacuum to the constructed cavity. A malleable tacky tape is placed in this groove and along the inner edge on the top side of the picture frame spacer plate. This tacky tape creates a seal between the spacer plate and the polyimide film diaphragm creating the sealed cavity in which the resin charge and carbon fiber preform are enclosed. After the diaphragm is placed onto the tacky tape seal, the picture frame clamping plate is positioned onto the mold assembly and bolted down tightly compressing the tacky tape and silicone rubber seals.

After the mold has been sealed, a vacuum is applied to about 400 millitor. The mold is then placed into a mechanical press and a thermocouple in the base plate of the mold is connected to a Camille™ data acquisition unit. An anvil is then placed on top of the diaphragm and the mold program is started. The mold program used in the manufacture of the panel is as follows:

| Duration (min) | Temperature (° C.) | Pressure (psi) |
| --- | --- | --- |
| 30 | 290 | 15 |
| 1 | 290 | 32 |
| 1049 | 290 | 50 |
| 120 | 320 | 50 |
| 180 | 350 | 50 |

Analysis of the Composite Panel

After completing the cure in the press, the composite is cut to observe the quality of the consolidation. The cross section reveals no voids. The composite has an average part thickness of (0.3454) centimeter (0.1359 inch) and a fiber volume of 52.1 percent. A sample of the composite is analyzed by DMTA at a heating rate of 5° C. per minute to 500° C. using a frequency of 1 Hz. This analysis showed a tan delta peak at 342° C., which was taken as the glass transition temperature for the composite. A portion of the composite is mechanically tested for short beam shear strength using ASTM D-2344 (1992). Ten samples are cut from the composite and tested. The results of these tests showed that the composite has a short beam shear strength of 7240 psi with a standard deviation of 384 psi and a coefficient of variation of 5.30 percent.

EXAMPLE 4

Preparation of Phenylethynyl Terminated Resin Composition Number 4:

1-methyl-2-pyrrolidinone (61.336 grams) is added to a stirred, 250 milliliter round bottom flask equipped with a nitrogen purge, water cooled condenser, thermometer and heating mantel connected to a temperature controller. 1,3 bis(3-aminophenoxy)benzene (32 grams; 0.1094 moles) is next added to the round bottom flask. After the 1,3 bis(3-aminophenoxy)benzene has dissolved, a stirred slurry consisting of 112.046 grams of 1-methyl-2-pyrrolidinone, 32.608 grams of 4-phenylethynyl phthalic anhydride (0.1314 moles) and 9.551 grams of 1,2,4,5-benzenetetracarboxylic dianhydride (0.0438 moles) are added to the 250 milliliter flask. After the addition of the slurry, the mixture self heats to 45° C. and is clear. This solution is then heated to 70° C. where it is maintained for 24 hours. After 24 hours at 70° C., a 15 milliliter Dean-Stark distillation receiver filled with toluene is installed on the top of the round bottom flask beneath the condenser. Toluene (33.858 grams) is also added directly to the 250 milliliter round bottom flask. This solution is then heated to 160° C. After 14 hours at 160° C., the Dean-Stark receiver contains a bottom layer of 7.5 milliliters. This is drained along with the total contents of the Dean-Stark receiver. The solution in the round bottom flask is then heated to 200° C. where it is maintained for 2 hours. During this time the Dean-Stark receiver is drained an additional three times. After 2 hours at 200° C., the solution is cooled to 70° C. and then slowly poured into an operating blender containing 350 milliliters of water. After blending for 15 minutes, the solution is filtered using a fritted glass filtering funnel (ASTM 10–15M). The wet filter cake obtained is placed back in the blender and fresh water is added. After the addition of the water, the total contents in the blender is approximately 650 milliliters. After blending for 15 minutes, the solution is filtered using the same fritted glass filtering funnel. The filter cake obtained from the second filtration is added back to the blender along with more fresh water. The total volume in the blender after this addition is approximately 650 milliliters. This solution is blended for 15 minutes and then filtered. The filter cake obtained is placed in a 110° C., forced air convection oven for 3 hours. This material is then ground to a coarse powder and placed in a vacuum oven where drying is continued for an additional 14 hours at 122° C. and 12 hours at 213° C. The dried resin is then allowed to cool to room temperature under vacuum. After cooling to room temperature, the resin is reground to a fine powder using a mortar and pestle.

Analysis of Phenylethynyl Terminated Resin Number 4:

DSC analysis is conducted for an 11.28 milligram sample of the resin prepared from above using a heating rate of 10° C. per minute and a nitrogen purge of 35 cubic centimeters per minute. This DSC analysis showed that the resin prepared has a glass transition temperature of 110° C. and a cure exotherm with an onset of 338° C., peak of 384° C. and a total energy of 253 joules per gram. Viscosity measurements for the resin are conducted using 2 inch parallel plates at 100 rads per second, 10 percent strain and a heating rate of 2° C. per minute. These measurements showed a minimum viscosity of 60 to 70 centipoise over the temperature range of 530° F. (277° C.) to 600° F. (316° C.).

Preparation and Analysis of Cured Resin:

The above resin (3.484 grams), contained in an aluminum pan, is placed in a convection oven which is preheated to 300° C. After 18.5 hours at 300° C., the oven temperature is increased to 350° C. After the resin has been in the 350° C. oven for 2 hours, it is removed and cooled to room temperature. On cooling to room temperature, a cured resin casting is obtained from the aluminum pan. Weighing of this casting shows that a 0.96 percent weight loss has occurred during cure. A 26.0 milligram sample of the casting was taken for DSC analysis at a heating rate of 10° C. per minute and using a nitrogen purge of 35 cubic centimeters per minute. This analysis showed an inflection at 261 ° C. which was taken as the glass transition temperature for the cured polymer.

Preparation of a Carbon Fiber Reinforced Composite Using Phenylethynyl Terminated Resin Number 4:

The infusion resin flow mold used to prepare the composite is the same as that used in Example 1. Based on the preform weight and the desired fiber volume of 53 percent, 42.16 grams of powdered resin is used. This powdered phenylethynyl terminated resin is the same as that prepared from above using a stoichiometric imbalance of diamine to dianhydride with phenylethynyl phthalic anhydride. The carbon fiber preform is then placed in the mold on top of the powdered resin. The carbon fiber used in the manufacture of the composite is an IM7, 6K, GP, 4HS with an areal weight of 200.2 grams/m$^2$. The carbon fiber is cut to 5 inches×7 inches, stacked by aligning each ply using the fabric tracers, and then sewn together to fix the orientation. The weight of this sewn, 16-ply preform is 68.41 grams. On the top side of the spacer plate is a machined groove which accommodates a 1/16-inch PEEK tube which is used to apply vacuum to the constructed cavity. A malleable tacky tape is placed in this groove and along the inner edge on the top side of the picture frame spacer is plate. This tacky tape creates a seal between the spacer plate and the polyimide film diaphragm creating the sealed cavity in which the resin charge and carbon fiber preform are enclosed. After the diaphragm is placed onto the tacky tape seal, the picture frame clamping plate is positioned onto the mold assembly and bolted down tightly, compressing the tacky tape and silicone rubber seals.

After the mold has been sealed, a vacuum is applied to about 400 millitor. The mold is then placed into a mechanical press and a thermocouple in the baseplate of the mold is connected to a Camille™ data acquisition unit. An anvil is then placed on top of the diaphragm and the mold program is started. The mold program used in the manufacture of the panel is as follows:

| Duration (min) | Temperature (° C.) | Pressure (psi) |
|---|---|---|
| 10 | 290 | 15 |
| 950 | 290 | 150 |
| 120 | 320 | 150 |
| 120 | 350 | 150 |

Analysis of the Composite Panel

After completing the cure in the press, the composite is cut to observe the quality of the consolidation. The cross section reveals no voids. The composite has an average part thickness of 0.313 centimeter (0.123 inch) and a fiber volume of 57.5 percent. A sample of the composite is analyzed by DSC analysis at a heating rate of 10° C. per minute and using a nitrogen purge of 35 cubic centimeters per minute. This analysis showed an inflection at 240° C. which was taken as the glass transition temperature for the composite.

What is claimed is:
1. A compound of the formula:

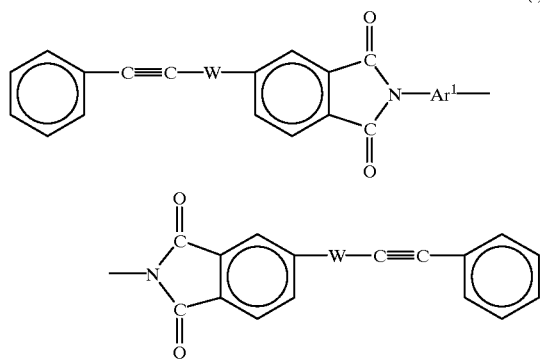

(I)

wherein Ar¹ is independently in each occurrence

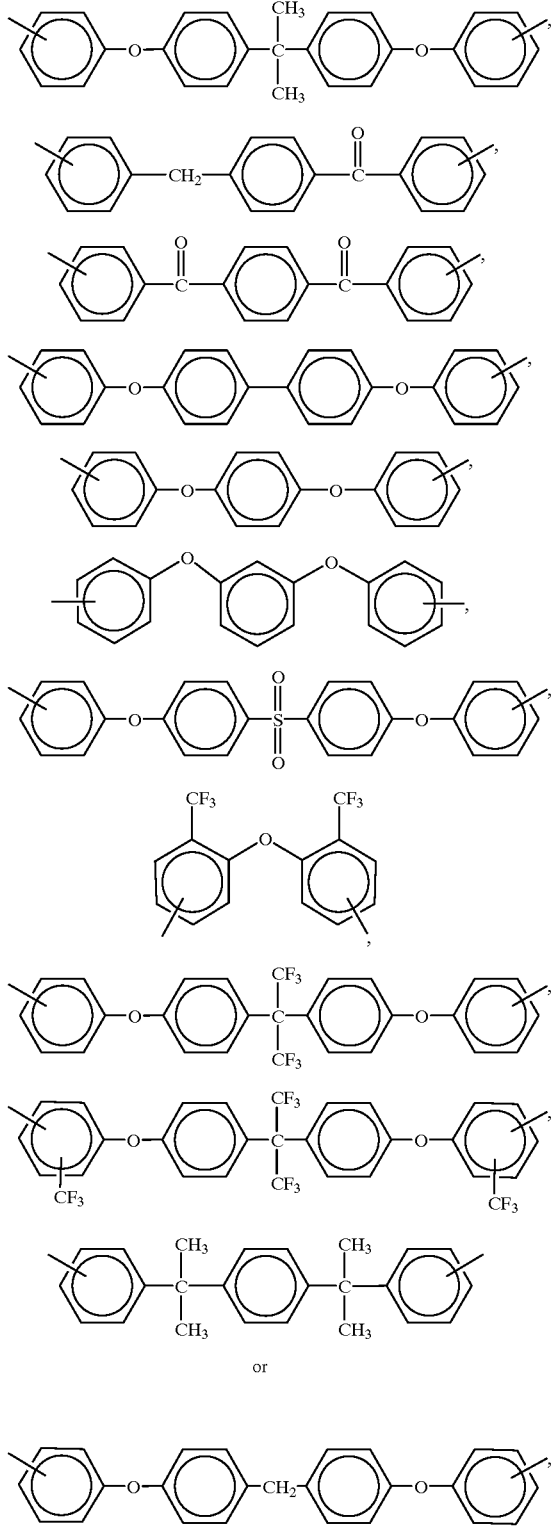

and

W is independently in each occurrence a bond,
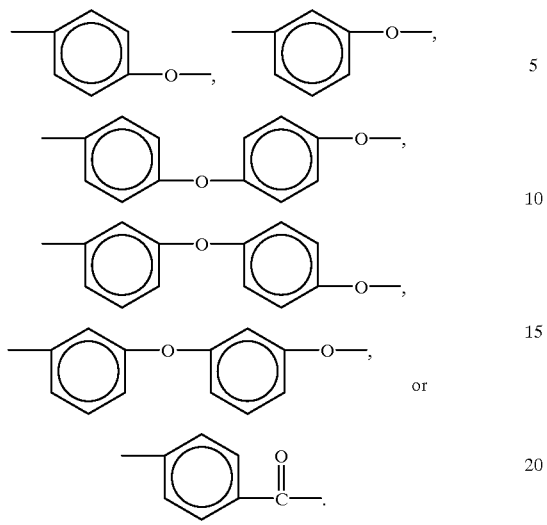
or
2. The compound of claim 1 wherein $Ar^1$ is independently in each occurrence:
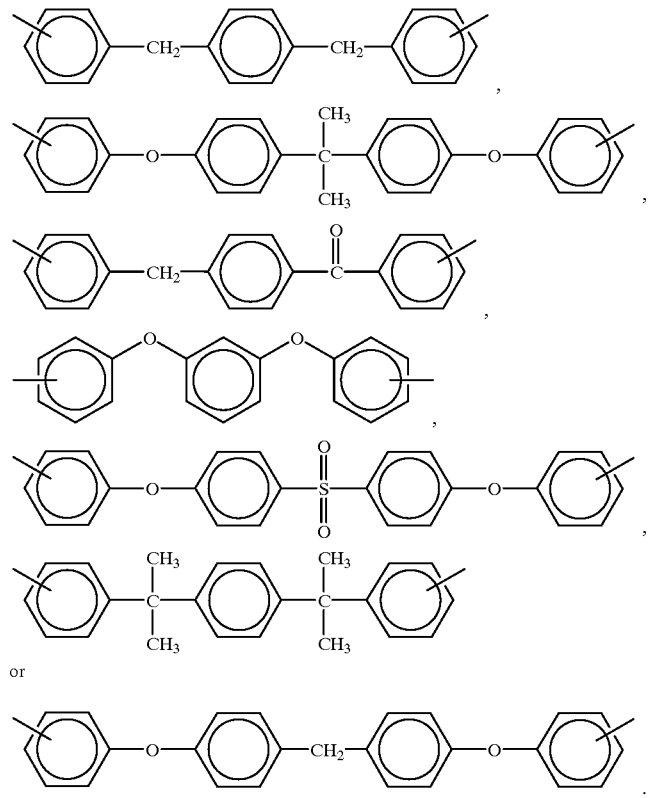
or
3. The compound of claim 1 wherein W is a single bond.
4. The compound of claim 3 wherein W is a single bond.
5. The compound of claim 1 of the formula:

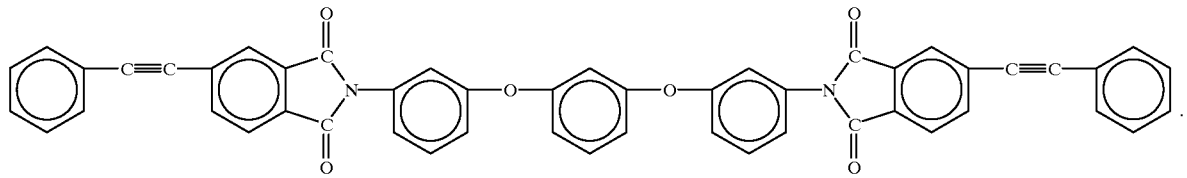

6. The compound of claim 1 of the formula:

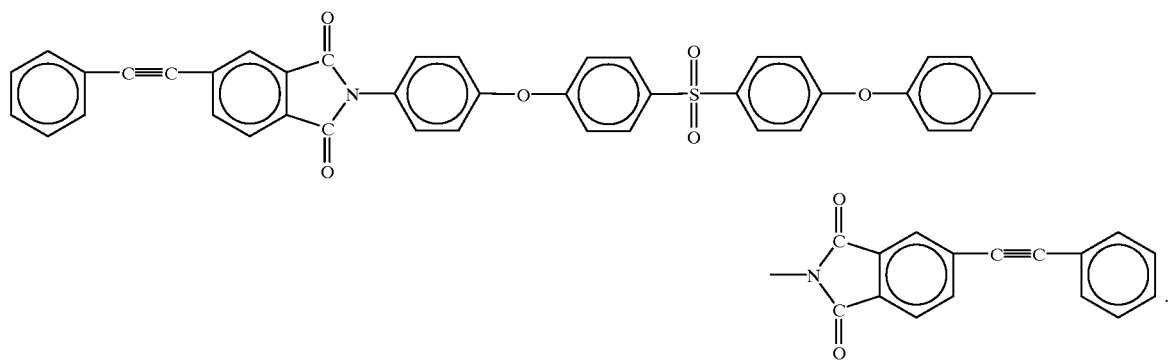

7. The compound of claim 1 of the formula:

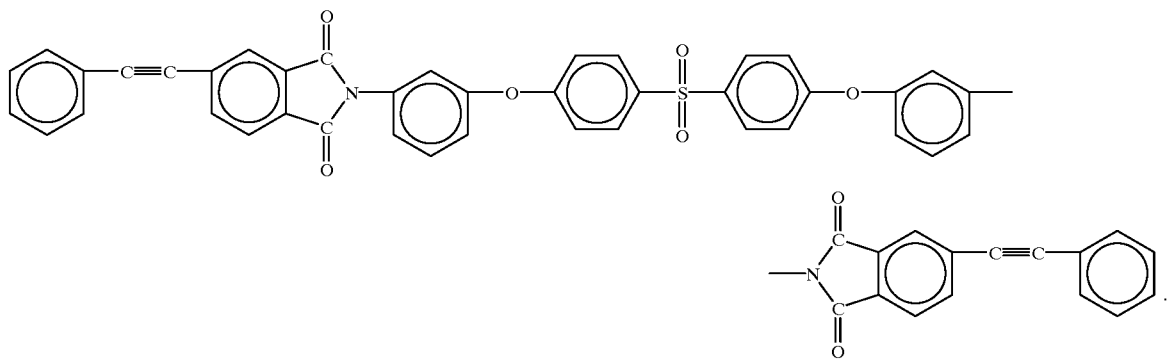

8. A cured polymer obtained by heating a plurality of the compounds of claim 1, optionally with other oligomers or polymers having terminal phenylethynyl groups.

9. A cured polymer obtained by heating a quantity of resin comprising the compound of claim 1 to at least 280° C. but to no greater than 400° C. for a time sufficient to cause the resin to cure.

10. A process for preparing a thermosetting resin composition comprising reacting a compound of the formula $NH_2$—$Ar^2$—$NH_2$, a phenylethynyl-terminated phthalic anhydride, and a dianhydride, and optionally, a triamine compound in molar proportions so that at least 10 percent by weight of the compositions is a compound of the formula:

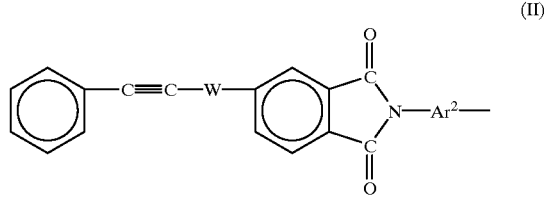

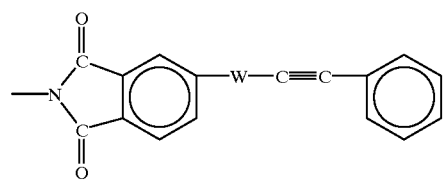

(II)

wherein Ar² is independently in each occurrence

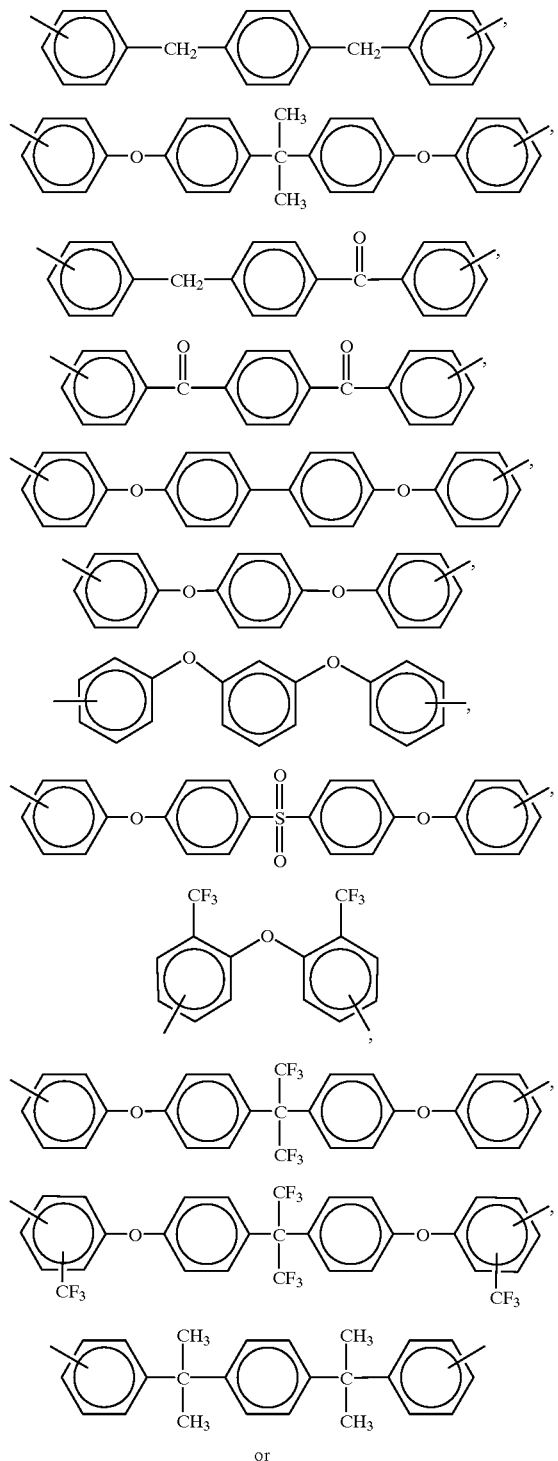

or

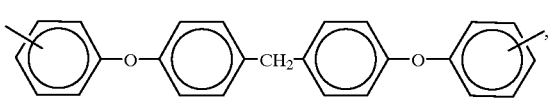

and

W is independently in each occurrence a bond,

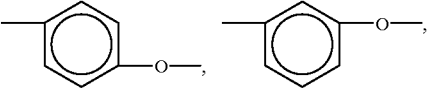

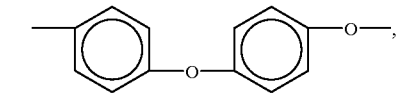

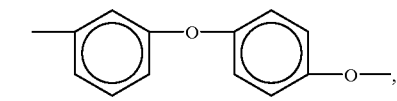

or

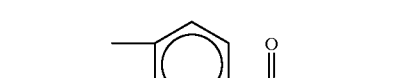

11. A process for preparing a thermosetting resin composition comprising reacting a compound of the formula:

a phenylethynyl-terminated phthalic anhydride, and a dianhydride, and optionally, a triamine compound in molar proportions so that at least 10 percent by weight of the composition is a compound of the formula:

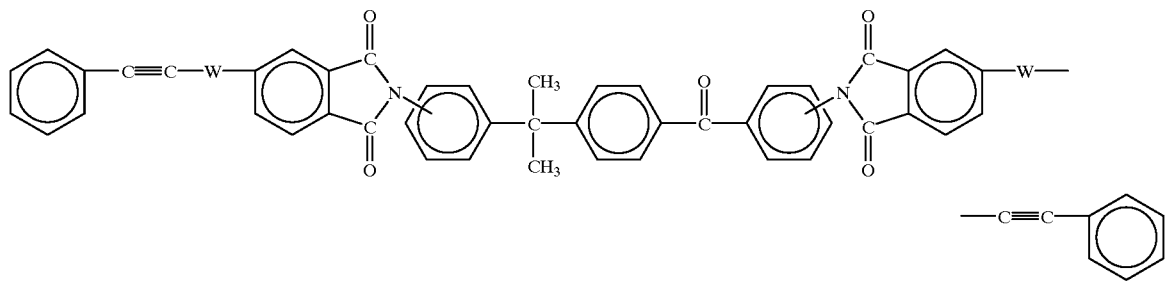

wherein W is independently in each occurrence a bond,

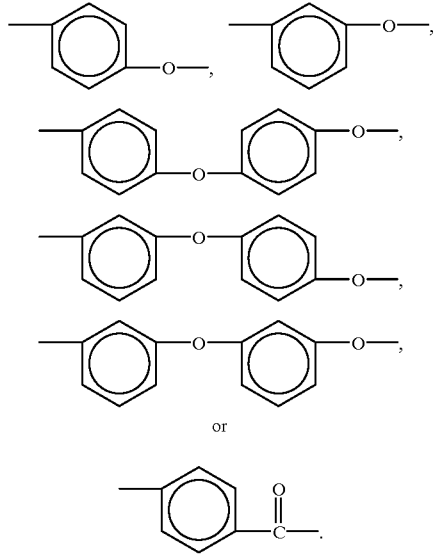

or

12. A process for preparing a composite article, comprising:

(a) placing a preform in a mold;

(b) contacting the preform with a thermosetting resin composition having a melt viscosity of less than 1000 centipoise at a temperature above its melting point;

(c) heating and compressing the resin composition and preform under conditions sufficient to cause the composition to saturate the preform and then cure, thereby forming the article; and (d) cooling the mold and removing the article from the mold;

wherein the resin composition comprises at least 10 weight percent of a compound of the formula:

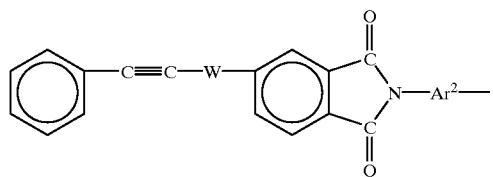

(II)

-continued

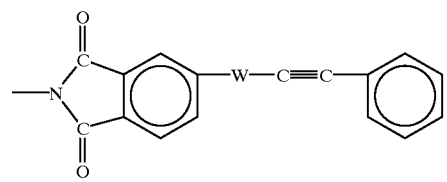

wherein $Ar^2$ is independently in each occurrence

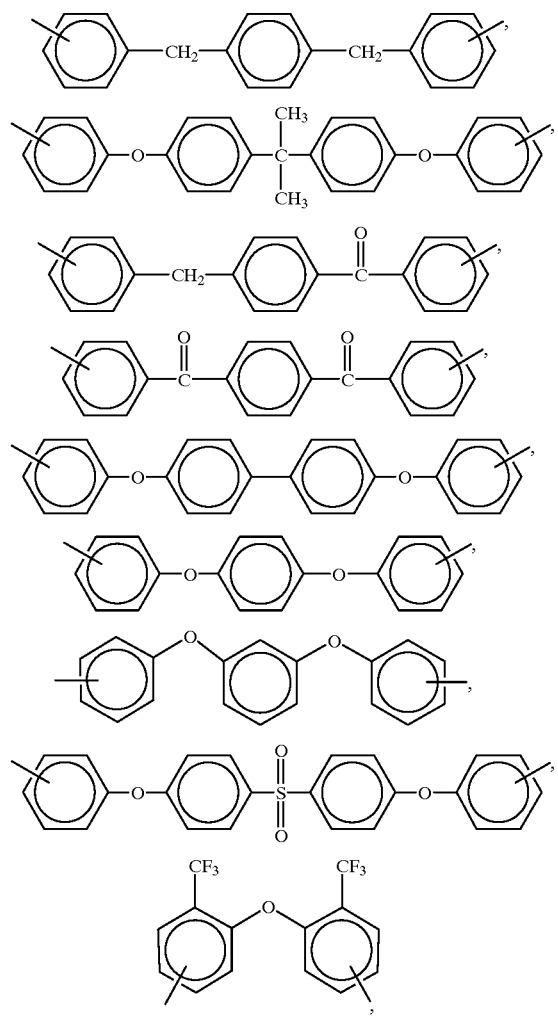

-continued
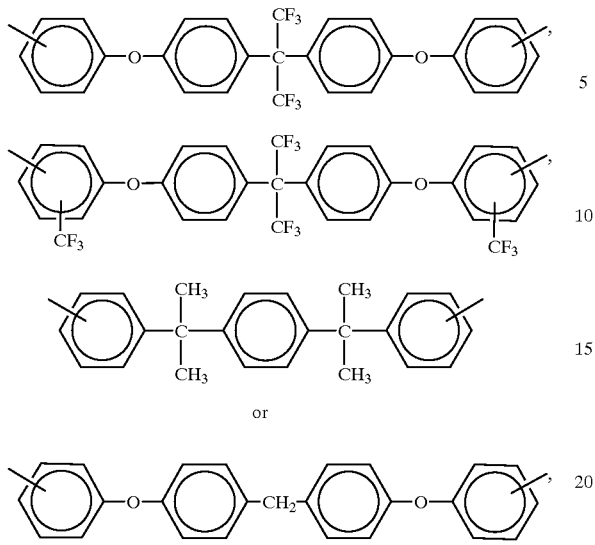
and
W is independently in each occurrence a bond,
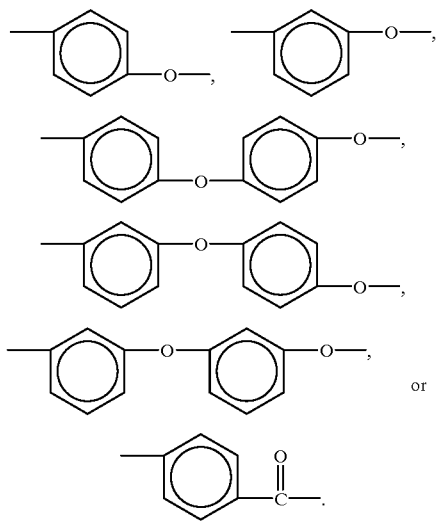
13. The process of claim 12 wherein $Ar^2$ is independently in each occurrence selected from:
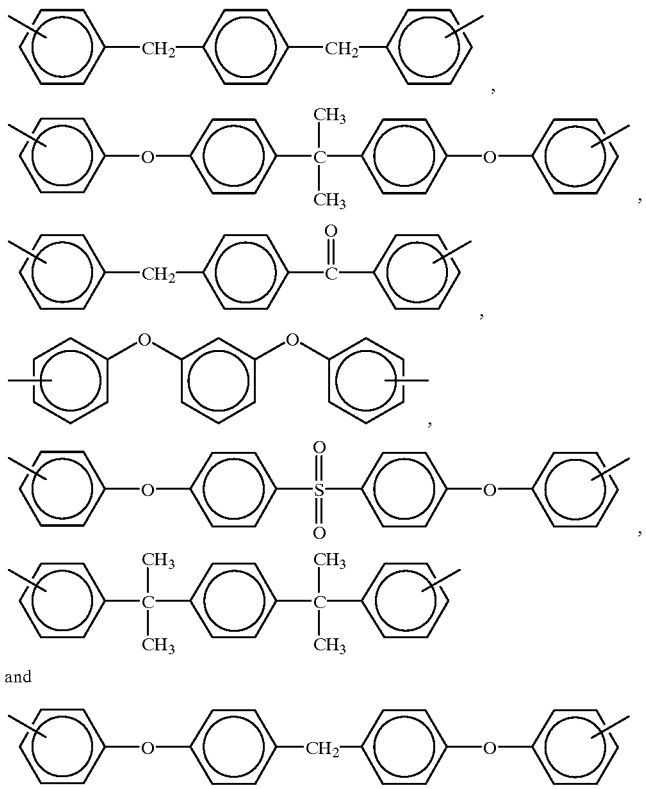
14. The process of claim 12 wherein W is a single bond.
15. The process of claim 13 wherein W is a single bond.
16. The process of claim 12 wherein the compound is of the formula:

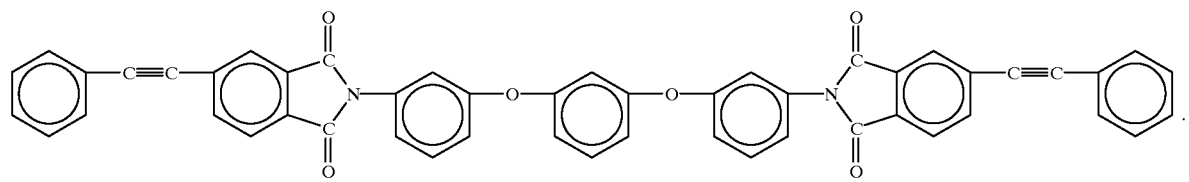
17. The process of claim 12 wherein the compound is of the formula:
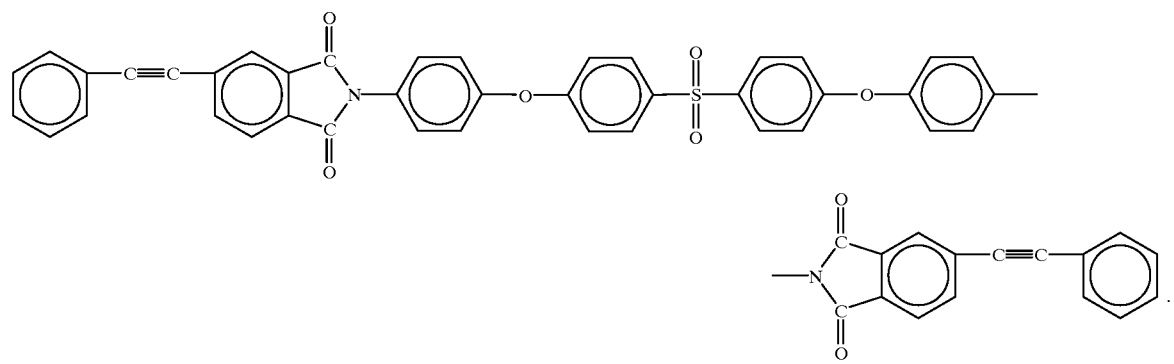
18. The process of claim 12 wherein the compound is of the formula:
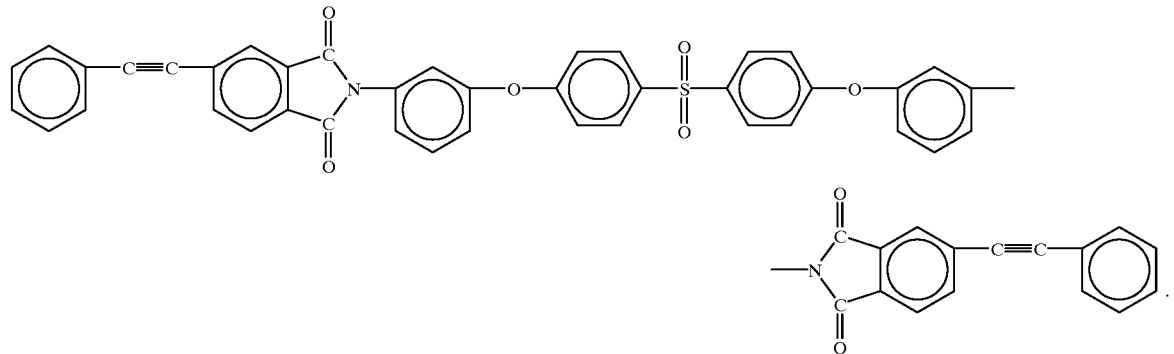
19. The cured, composite article obtained from the process of claim 12.
* * * * *